(12) United States Patent
Grob et al.

(10) Patent No.: US 9,131,895 B2
(45) Date of Patent: Sep. 15, 2015

(54) DISPOSABLE ELECTRODE FOR ELECTRO-STIMULATION

(75) Inventors: Timon Rutger Grob, Geldrop (NL); Rudolf Maria Jozef Voncken, Eindhoven (NL); Antonius Wilhelmus Maria De Laat, Den Dungen (NL); Judith Petra Huurdeman, Beek (NL); Ronaldus Mathias Hubertus Steijvers, NederWeert (NL); Lucas Johannes Anna Maria Beckers, Veldhoven (NL); Michael Johan Ferdinand Marie Ter Laak, Leende (NL); Steven Ernest Franklin, Eindhoven (NL); Sean Scott Wheelhouse, Orem, UT (US)

(73) Assignee: Koninklijke Philips N.V., Eindhoven (NL)

( * ) Notice: Subject to any disclaimer, the term of this patent is extended or adjusted under 35 U.S.C. 154(b) by 194 days.

(21) Appl. No.: 13/806,278

(22) PCT Filed: Jun. 29, 2011

(86) PCT No.: PCT/IB2011/052866
§ 371 (c)(1),
(2), (4) Date: Apr. 5, 2013

(87) PCT Pub. No.: WO2012/001643
PCT Pub. Date: Jan. 5, 2012

(65) Prior Publication Data
US 2013/0197341 A1    Aug. 1, 2013

Related U.S. Application Data

(60) Provisional application No. 61/361,032, filed on Jul. 2, 2010.

(51) Int. Cl.
*A61B 5/0408* (2006.01)
*A61N 1/04* (2006.01)
(Continued)

(52) U.S. Cl.
CPC ............... *A61B 5/6832* (2013.01); *A61B 5/04* (2013.01); *A61N 1/048* (2013.01); *A61N 1/0452* (2013.01);
(Continued)

(58) Field of Classification Search
CPC . A61B 5/04087; A61N 1/0452; A61N 1/0456
USPC ........... 600/391, 392, 394; 607/149, 152, 153
See application file for complete search history.

(56) References Cited

U.S. PATENT DOCUMENTS 3,606,881 A * 9/1971 Woodson ........................ 600/392
4,117,846 A * 10/1978 Williams ........................ 606/32
(Continued)

FOREIGN PATENT DOCUMENTS

CN    86104687 A    1/1988

*Primary Examiner* — Lee S Cohen

(57) ABSTRACT

An electrode configured to provide electrical contact with a subject's skin and includes a conductive layer and a gel layer. The conductive layer spreads current and transmits electrical signals to and/or receives electrical signals from the subject's skin and has a first conductive surface through which electrical signals are transmitted to and/or received from the subject's skin. The first conductive surface is on a side of the conductive layer that faces toward the subject's skin if the electrode is installed on the subject. The gel layer is formed on the same side of the conductive layer as the first conductive surface. The gel layer has a first interface surface that directly contacts the subject's skin if the electrode is installed on the subject, and to conduct electrical signals between the subject's skin and the first conductive surface. The first interface surface has a surface area larger than that of the first conductive surface.

15 Claims, 10 Drawing Sheets

(51) Int. Cl.
*A61B 5/00* (2006.01)
*A61B 5/04* (2006.01)

(52) U.S. Cl.
CPC ............ *A61N 1/0456* (2013.01); *A61N 1/0472* (2013.01); *A61N 1/0488* (2013.01); *A61N 1/0492* (2013.01); *A61B 5/04087* (2013.01); *A61N 1/0408* (2013.01); *A61N 1/0496* (2013.01); *Y10T 29/49204* (2015.01)

(56) References Cited

U.S. PATENT DOCUMENTS

| | | | | |
|---|---|---|---|---|
| 4,259,965 | A * | 4/1981 | Fukuda et al. | 600/392 |
| 4,300,575 | A * | 11/1981 | Wilson | 607/152 |
| 4,570,637 | A * | 2/1986 | Gomes et al. | 600/395 |
| 4,617,935 | A * | 10/1986 | Cartmell et al. | 600/392 |
| 4,653,503 | A * | 3/1987 | Heath | 600/391 |
| 4,763,660 | A * | 8/1988 | Kroll et al. | 600/391 |
| 4,798,642 | A * | 1/1989 | Craighead et al. | 156/252 |
| 4,838,273 | A | 6/1989 | Cartmell | |
| 4,926,878 | A | 5/1990 | Snedeker | |
| 4,934,383 | A * | 6/1990 | Glumac | 607/152 |
| 4,979,517 | A | 12/1990 | Grossman | |
| 5,042,144 | A * | 8/1991 | Shimada et al. | 29/825 |
| 5,265,579 | A * | 11/1993 | Ferrari | 600/391 |
| 5,355,883 | A | 10/1994 | Ascher | |
| 6,115,625 | A * | 9/2000 | Heard et al. | 600/391 |
| 6,418,333 | B1 * | 7/2002 | Axelgaard | 600/391 |
| 6,745,082 | B2 | 6/2004 | Axelgaard | |
| 6,795,722 | B2 * | 9/2004 | Sheraton et al. | 600/391 |
| 7,079,884 | B1 * | 7/2006 | Epstein | 600/391 |
| 7,403,807 | B2 * | 7/2008 | Dupelle et al. | 600/372 |
| 2009/0043185 | A1 | 2/2009 | McAdams | |
| 2013/0066412 | A1 | 3/2013 | Van Der Beek et al. | |

* cited by examiner

DISPOSABLE ELECTRODE FOR ELECTRO-STIMULATION

The invention relates to an electrode for use in medical applications (e.g., stimulations and physiological parameters monitoring), and a method of manufacture therefor.

Electrodes that provide electrical contact with a patient's skin to transfer electrical signals between the patient's skin and a medical device are known. Such electrodes typically have a hydrogel layer and a conductive layer. The hydrogel layer is used to adhere the electrode to the patient's skin. However, using only the hydrogel as an adhesion mechanism may not be sufficient. For example, the adhesive properties of the hydrogel may not be reliable when the electrode is positioned at certain locations on the patient's body. Furthermore, using the hydrogel for both conductivity and adhesion during overnight stimulation may accelerate the dehydration thereof, thus decreasing the conductivity and effectiveness of the electrode.

Furthermore, the electrodes typically have a highly conductive layer and a hydrogel or liquid gel layer that are of the same size. However, this configuration may create "hot spots" of high current density, or high-current concentrations at a specific location, that can lead to an irritating and/or uncomfortable burning sensation on the skin.

One aspect of the invention relates to an electrode configured to provide electrical contact with a subject's skin. The electrode includes a conductive layer configured to spread current in the electrode and transmit electrical signals to and/or receive electrical signals from the subject's skin. The conductive layer has a first conductive surface through which electrical signals are transmitted to and/or received from the subject's skin. The first conductive surface is on a side of the conductive layer that faces toward the skin of the subject if the electrode is installed on the subject. The electrode also includes a gel layer formed on the same side of the conductive layer as the first conductive surface. The gel layer has a first interface surface configured to directly contact the subject's skin if the electrode is installed on the subject, and to conduct electrical signals between the subject's skin and the first conductive surface. The first interface surface has a surface area larger than that of the first conductive surface.

Another aspect relates to an electrode configured to provide electrical contact with a subject's skin. The electrode includes means for transmitting electrical signals to and/or receive electrical signals from the subject's skin. The transmission is provided by a conductive layer having a first conductive surface configured to transmit electrical signals to and/or receive electrical signals from the subject's skin. The first conductive surface is on a side of the conductive layer that faces toward the skin of the subject if the electrode is installed on the subject. The electrode also includes means for conducting electric signals between the subject's skin and the first conductive surface. The conduction is provided by a gel layer formed on the same side of the conductive layer as the first conductive surface. The gel layer has a first interface surface configured to directly contact the subject's skin if the electrode is installed on the subject. The first interface surface has a surface area larger than that of the first conductive surface.

Another aspect relates to a method of manufacturing an electrode for providing electrical contact with a subject's skin. The method includes forming a conductive layer configured to transmit electrical signals to and/or receive electrical signals from the subject's skin. The conductive layer has a first conductive surface through which electrical signals are transmitted to and/or received from the subject's skin. The first conductive surface is on a side of the conductive layer that faces toward the skin of the subject if the electrode is installed on the subject. The method also includes forming a gel layer on the same side of the conductive layer as the first conductive surface. The gel layer has a first interface surface configured to directly contact the subject's skin if the electrode is installed on the subject, and to conduct electrical signals between the subject's skin and the first conductive surface. The first interface surface has a surface area larger than that of the first conductive surface.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
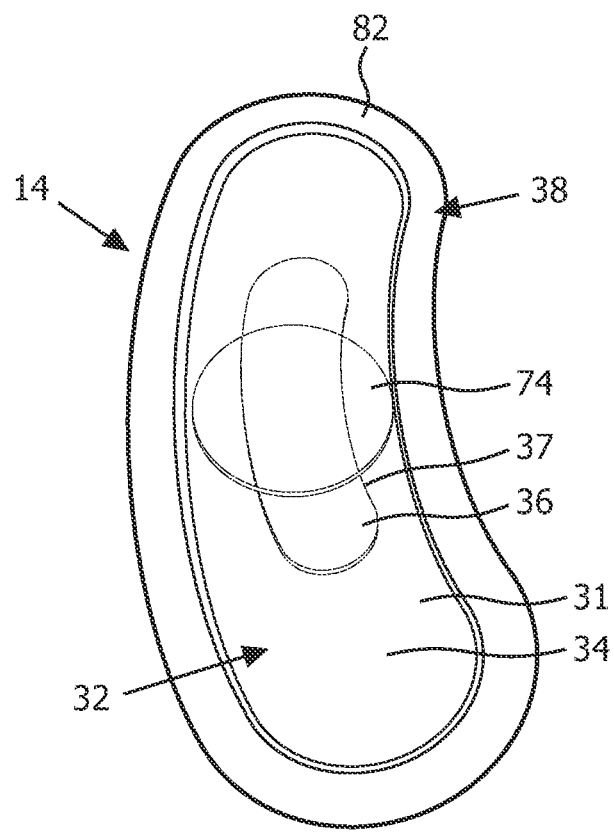
FIG. 1 illustrates a front layer of an electrode in accordance with an embodiment.

FIG. 1 illustrates an electrode 14 that is configured to provide electrical contact with a subject's skin. The electrode 14 includes a conductive layer 36, which may be a current spreader, configured to spread current over the electrode and to transmit electrical signals to and/or receive electrical signals from the subject's skin. The conductive layer 36 has a first conductive surface 37 through which electrical signals are transmitted to and/or received from the subject's skin. In some embodiments, the first conductive surface 37 does not directly contact the subject's skin. The first conductive surface 37 is on a side of the conductive layer 36 that faces toward the skin of the subject if the electrode is installed on the subject. The electrode 14 also includes a gel layer 34 formed on the same side of the conductive layer 36 as the first conductive surface 37. The gel layer 34 has a first interface surface 31 configured to directly contact the subject's skin if the electrode 14 is installed on the subject. The gel layer 34 is also configured to conduct electrical signals between the subject's skin and the first conductive surface 37. The first interface surface 31 has a surface area larger than that of the first conductive surface 37. In one embodiment, the gel layer 34 and the conductive layer 36 are formed such that a footprint of the first interface surface 31 overlaps the entirety of a footprint of the first conductive surface 37.

In the illustrated embodiment, the electrode 14 also has a non-conductive front portion, which may be an adhesive layer 38, having a second interface surface 82 configured to contact and adhere to the subject's skin. The adhesive layer 38 and the gel layer 34 may form a front layer 32 of the electrode 14, the front layer 32 being configured to contact the subject's skin. The adhesive layer 38 may be positioned relative to the gel layer 34 such that the first interface surface 31 is flush with the second interface surface 82. Alternatively, in some embodiments, the adhesive layer 38 may be positioned relative to the gel layer 34 such that the first interface surface 31 is not flush with the second interface surface 82 but rather is positioned higher than the second interface surface 82. In the illustrated embodiment, the adhesive layer 38 generally surrounds a periphery of the gel layer 34. However, this is configuration is not intended to be limiting and the adhesive layer 38 may be placed in different configurations relative to the gel layer 34. For example, the adhesive layer 38 may partially surround a periphery of the gel layer 34 or may be placed at various locations near the gel layer 34. The electrode 14 may also optionally have adhesive material on both sides thereof.

Figure 2:
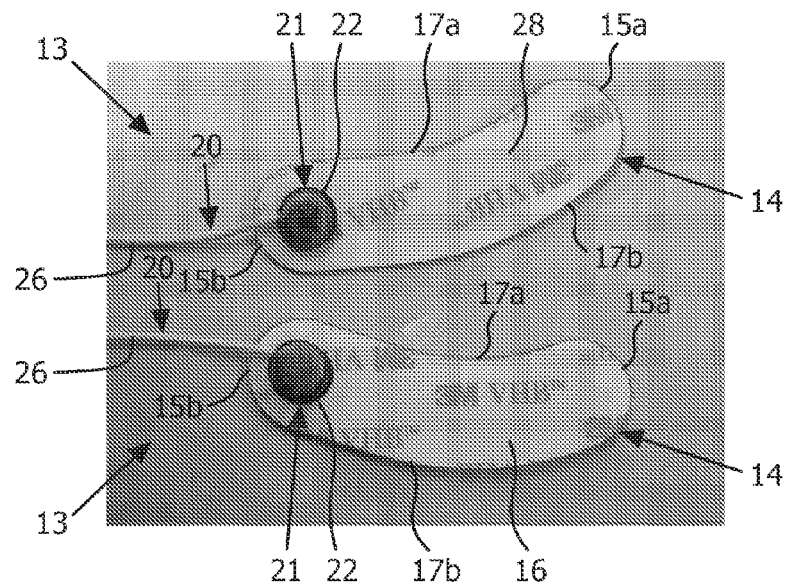
FIG. 2 illustrates a base pad of the electrode in accordance with one embodiment.
Figure 5:
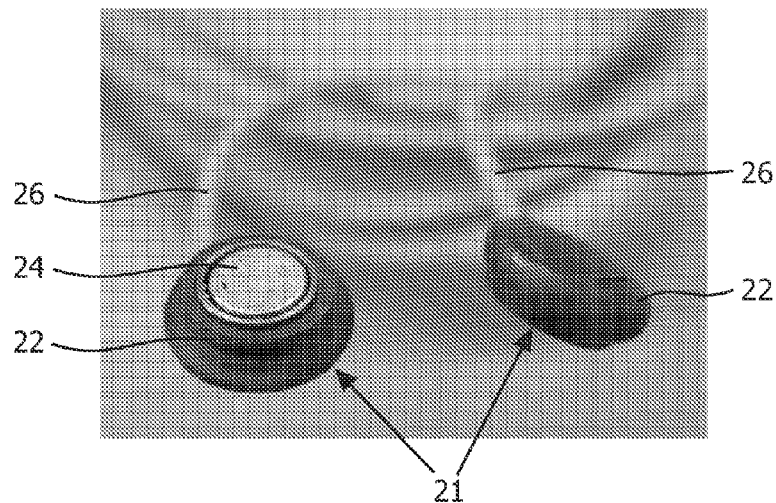
FIG. 5 illustrates a detailed view of an attachment structure of the connector assembly in accordance with one embodiment.
Figure 6:
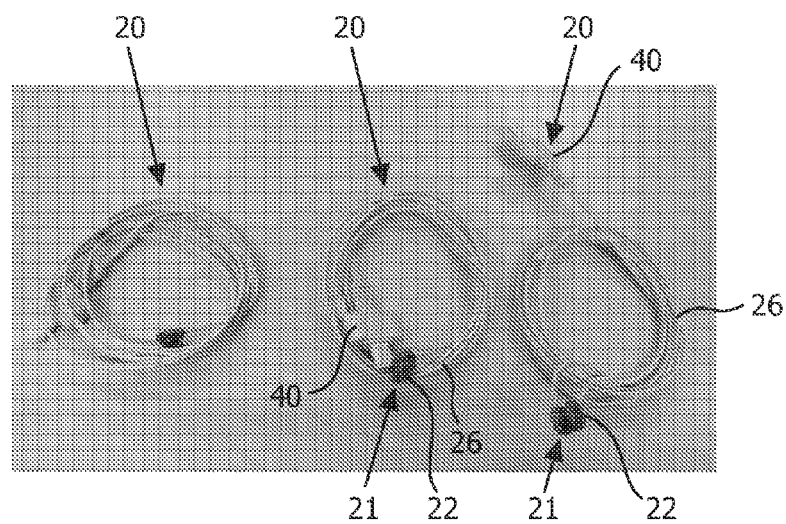
FIG. 6 illustrates the connector assembly in accordance with one embodiment.

In one embodiment, the electrode 14 includes an electrode base pad 16 (see FIG. 3b) having a first contact surface 18 (see FIG. 3b) on a side of the electrode 14 opposite the first interface surface 31. The first contact surface 18 may be configured to connect to a second contact surface 24 (see FIG. 5) of a connector assembly 20 (see FIG. 6). The electrode 14 may be part of an electrode assembly 13, an embodiment of which is illustrated in FIG. 2. In the illustrated embodiment, the electrode assembly 13 includes the electrode 14 and the connector assembly 20 configured to electrically connect the electrode 14 to an external electrical apparatus (not shown) such that electrical signals can be transferred between the subject's skin and the external electrical apparatus. The external electrical apparatus can be of any type of monitoring or stimulation devices, such as, just for example, electrograph (ECG) devices, electroencephalograph devices, electromyography devices, transcutaneous electrical nerve stimulation devices, electrical muscle stimulation devices, neuromuscular stimulation devices, or functional electrical stimulation devices. The connector assembly 20 includes an attachment structure 21 having a housing 22 and the second contact surface 24 (see FIG. 5). The connector assembly 20 will be described in more detail later.

Figure 15:
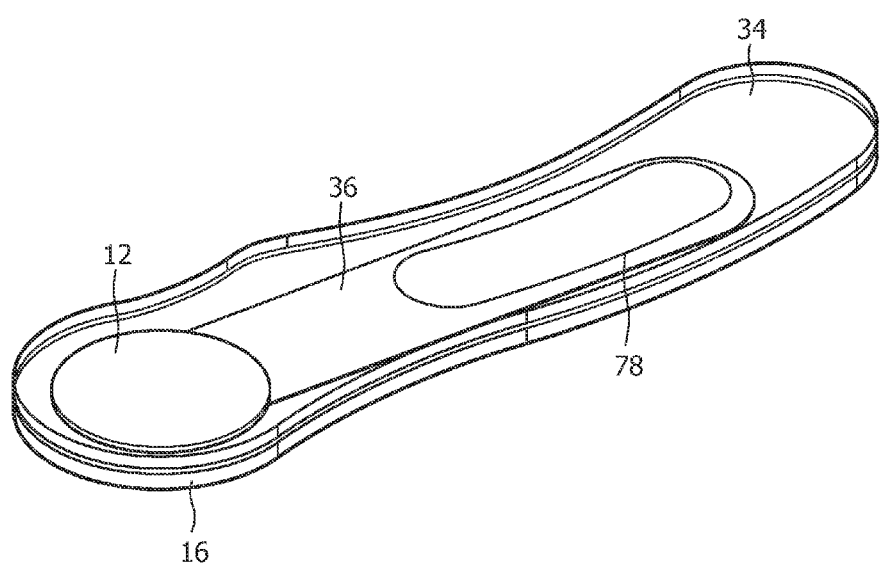
FIG. 15 illustrates the electrode of the embodiment of FIG. 14.

In the embodiment shown in FIG. 2, the electrode 14 includes curves or smoothly rounded bends that generally form a banana shape. That is, the electrode 14 may be rounded at ends 15a, 15b with arcuate sides 17a, 17b that form a generally arcuate body. Arcuate does not necessarily mean a perfect arc, but may refer to general curvature of the sides and/or body as a whole. The rounded ends 15a, 15b may connect with the arcuate sides 17a, 17b in a smooth manner (i.e., without sharp edges). In the embodiment shown in FIG. 3b, the ends 15a, 15b are generally curved in a convex shape away from latitudinal line B-B. In the illustrated embodiment, the arcuate side 17a is generally curved towards longitudinal line A-A in a concave shape and the arcuate side 17b is generally curved away from longitudinal line A-A in a convex shape. The curvature of the arcuate sides may vary along the length of the body. For example, in some embodiments, the arcuate sides may be defined by multiple curves or bends having various angles so that the arcuate sides 17a, 17b are spaced at different distances from each other along the length of the body. In such embodiments, the length or angle of curvature of the ends 15a, 15b may be different from one other. In some embodiments, the arcuate sides 17a, 17b of the arcuate body may be longer than the rounded ends 15a, 15b, thus forming a generally longitudinally extending body. However, the above description of the configuration, shape, and size of the electrode 14 is not intended to be limiting, and it is contemplated that the configuration, shape, and size of the electrode 14 may vary in other embodiments. For example, the electrode 14 may have an alternative generally arcuate shape as shown in the embodiment of FIG. 15.

The banana-shaped configuration of the electrode 14 shown in FIG. 2 may facilitate the positioning of the electrode 14 at various positions on the subject's body. For example, the curved banana-shape of the electrode 14 in one embodiment can facilitate the positioning of the electrode 14 behind the subject's ear, which is usually difficult due to the fact that one cannot easily see the side of one's head when attempting to apply the electrode 14 to the side of the head. However, it is contemplated that the electrode 14 may have other shapes, such as just, for example, circular, oval, or rectangular, and may have various sizes.

Figure 3A:
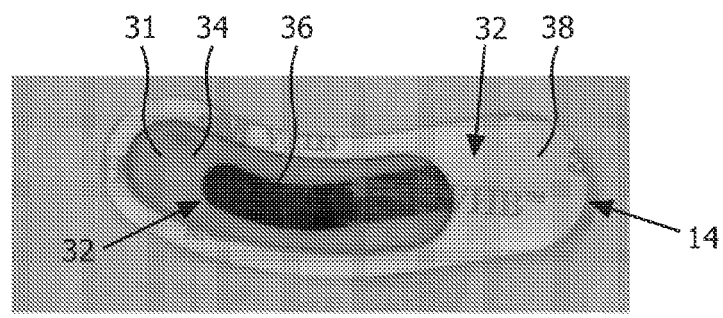
FIGS. 3a-3b illustrate a subject contact surface on a side of the electrode opposite the base pad and the base pad of the electrode, respectively, in accordance with one embodiment.
Figure 3B:
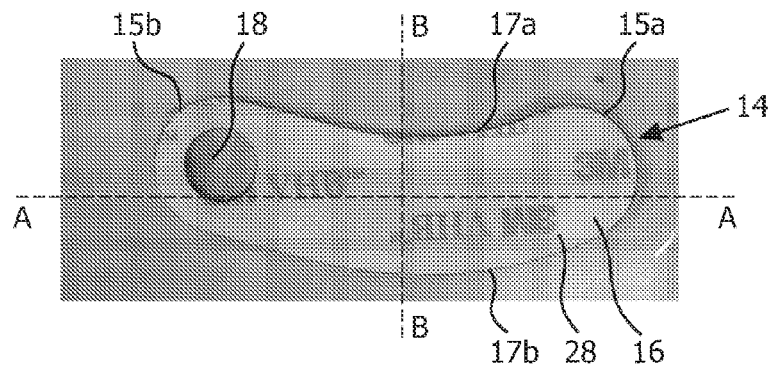

As shown in FIG. 3a and as mentioned above, the first interface surface 31 is configured to contact the subject's skin and may be defined by the gel layer 34. The gel layer 34 may be conductive and may facilitate the distribution of electric signals between the subject's skin and the electrode 14. The gel layer 34 may include an adhesive material to facilitate the connection between the electrode 14 and the subject's skin. Alternatively, the gel layer 34 may include no adhesive material. As mentioned above, the conductive layer 36 may be configured to distribute electric signals between the first contact surface 18 of the electrode base pad 16 and the first interface surface 31 defined by the gel layer 34. The conductive layer 36 may be made of, just for example, metallic foils, conductive polymers, graphitized or metalized cloth or wire mesh. The conductive layer 36 may generally have a similar shape as the gel layer 34. The conductive layer 36 may optionally be smaller than the gel layer 34. Alternatively, the conductive layer 36 may be the same size or may be larger than the gel layer 34.

The front layer 32 may also include the adhesive layer 38. The adhesive layer 38 may optionally be constructed of the same material as the electrode base pad 16. The adhesive layer 38 may be made of foam or other materials that provide padding to improve comfort for the subject. In one embodiment, the adhesive layer 38 may include an adhesive material that facilitates the connection between the electrode 14 and the subject's skin. It is contemplated that in some embodiments, the adhesive layer 38 can be eliminated, and the gel layer 34 may be an adhesive gel capable of adhering the electrode 14 to the subject's skin. In one embodiment, the adhesive layer 38 may be positioned around a periphery of the conductive gel layer. That is, an opening 80 (see FIG. 4) having a shape substantially similar to the gel layer 34's may be formed in the adhesive layer 38 and the gel layer 34 may be positioned within the opening 80 of the adhesive layer 38.

The electrode pad 14 may be provided with a plastic carrier or film to prevent inadvertent and/or premature adhesion of a patient's skin or other object to portions of the front layer 32. The plastic carrier may be removed prior to application of the electrode 14 to the subject's skin. The plastic carrier may be disposed on either one or both of the adhesive layer 38 and the gel layer 34 (in embodiments where the gel layer 34 is an adhesive gel). It is contemplated that the electrode 14 may be disposable. The electrode 14 may be adhered to the subject's skin when in use and after it is no longer needed, the electrode 14 may be peeled off from the subject's skin and disposed of. In one embodiment, the connector assembly 20 (see FIG. 6) used to connect the electrode 14 to the external electrical apparatus may be re-used with other electrodes 14.

Figure 4:
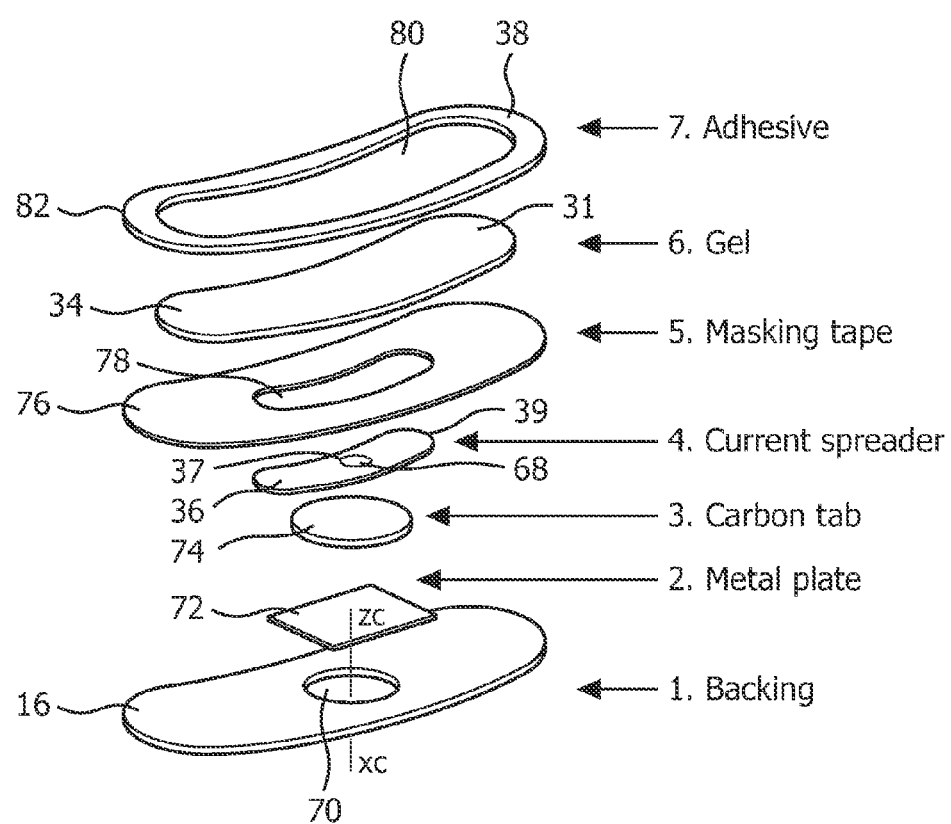
FIG. 4 is an exploded view of components of the electrode in accordance with an embodiment.

FIG. 4 shows an exploded view of the various layers or materials of the electrode 14 in accordance with one embodiment. In this embodiment, the electrode 14 includes the base pad 16 having an opening 70 configured to receive the second contact surface 24 of the connector assembly 20. In this embodiment, the base pad 16 is generally banana-shaped, although circles, rectangles, or other shapes are contemplated. The base pad 16 may include foam material, such as the polyolefin type made by Sekisui.

In the illustrated embodiment, a plate 72 is disposed on the base pad 16, wherein the first contact surface 18 is defined on the plate 72. That is, the first contact surface 18 may be a portion of the plate 72 that is exposed through the opening 70. In the illustrated embodiment, the plate 72 is rectangular. Alternatively, the plate 72 may be circular, banana-shaped, or may be other shapes. In this embodiment, the plate 72 is a metal plate, such as those made by Hasberg-Schneider GmbH. In some embodiments, the plate 72 may include a magnet or may include ferromagnetic material. In such embodiments, the plate 72 may include magnetic characteristics or may be magnetized to include magnetic characteristics that enables the plate 72 to be magnetically coupled to metals or other magnetic materials. In such embodiments, the second contact surface 24 of the connector assembly 20 may include metal.

A second conductive layer 74 may be disposed on the plate 72. The second conductive layer 74 may be configured to conduct electric signals between the conductive layer 36 and the first contact surface 18 defined on the metal plate 72 and may be made of carbon or other conductive materials. The second conductive layer 74 may be circular, rectangular, banana-shaped, or may be other shapes. The second conductive layer 74 may also include adhesive material that enables the second conductive layer 74 to be adhered to other portions of the electrode 14. The second conductive layer 74 may be a carbon disk, such as those made by SPI Supplies/Structure Probe, Inc.

The conductive layer 36 may be disposed on the second conductive layer 74 and may be configured to distribute electric signals between the second conductive layer 74 and the gel layer 34. In some embodiments, the conductive layer 36 may be disposed on the metal plate 72 and may define a portion of the first contact surface 18 such that when the second contact surface 24 of the connector assembly 20 is magnetically and electrically coupled to the first contact surface 18 of the metal plate 72, the conductive layer 36 is disposed between the metal plate 72 and the second contact surface 24 of the connector assembly 20. The conductive layer 36 may have edges 39. In the illustrated embodiment, the conductive layer 36 is generally banana-shaped. Alternatively, the conductive layer 36 may be circular, rectangular, or may be other shapes. The conductive layer 36 may include conductive materials such as those made by Exopack. An electrically insulating material 76, taking the form of a tape in this embodiment, may be provided with an opening 78 configured to receive or overlap the conductive layer 36. In some embodiments, the electrically insulating material 76 may include adhesive material. The insulating material 76 may be a double-sided tape having adhesives on both surfaces thereof, such as those made by Tesa Tape, Inc. The opening 78 may be shaped substantially similar and may also be sized substantially similar to the conductive layer 36. As such, the conductive layer 36 may be exposed through the opening 78. In the illustrated embodiment, the insulating material 76 is generally banana-shaped. Alternatively, the insulating material 76 may be circular, rectangular, or may be other shapes. Portions of the insulating material 76 may contact and adhere to portions of the base pad 16, thus retaining materials and layers therebetween.

The gel layer 34 may be disposed on the insulating material 76. In the illustrated embodiment, the gel layer 34 is generally banana-shaped. Alternatively, the gel layer 34 may be circular, rectangular, or may be other shapes. The gel layer 34 may include hydrogel materials, such as, just for example, the ARBO HRA5 gel made by Covidien. In the illustrated embodiment, the adhesive layer 38 includes the opening 80 configured to receive the gel layer 34. As mentioned above, in some embodiments, the adhesive layer 38 may be eliminated from the electrode 14 and the gel layer 34 may be used to adhere the electrode 14 to the subject's skin. In this embodiment, the adhesive layer 38 is provided with adhesive material, wherein the second interface surface 82 of the adhesive layer 38 contacts and adheres to the subject's skin. The adhesive layer 38 may include adhesive materials such as those made by Smith & Nephew. In one embodiment, the gel layer 34 may be received in the opening 80 of the adhesive layer 38 such that the adhesive layer 38 is flush with the gel layer 34. That is, the second interface surface 82 of the adhesive layer 38 may be substantially even with the first interface surface 31 of the gel layer 34 However, it is contemplated that in some embodiments, the adhesive layer 38 is not flush with the gel layer 34. For example, the adhesive layer 38 may be positioned relative to the gel layer 34 such that the first interface surface 31 of the gel layer 34 is at an elevated height relative to the second interface surface 82 of the adhesive layer 38. It should be appreciated, however, that the adhesive layer 38 may be positioned at various configurations relative to the gel layer 34 in other embodiments. It should also be appreciated that in some embodiments, the adhesive layer 38 does not surround the gel layer 34. That is, the adhesive layer 38 may be placed near the gel layer 34 but does not form a periphery around the gel layer 34. In some embodiments that have the non-conductive portion 38 with adhesive material, the gel layer 34 may optionally be non-adhesive. Forming the non-conductive portion 38 with adhesive material around the periphery of the gel layer 34 may improve the fixation or connection of the electrode 14 to the subject's skin and may also improve the conductive performance of the gel layer 34.

The size of the conductive layer 36 or the first interface surface 31 and the amount of electrical power that is applied during stimulation can significantly influence a subject's comfort. For example, in some situations, the subject may experience tingling or other sensations that may cause discomfort. These tingling sensations may be due to the stimulations of neurons that are incidentally stimulated along with the targeted muscles. Furthermore, subjects often experience the most discomfort at the leading edges of the electrode 14, also known as the "edge effect."

In the embodiment shown in FIG. 4, the gel layer 34 is shaped generally similar to the conductive layer 36 and has a larger size than the conductive layer 36 such that the gel layer 34 overlaps the conductive layer 36. The gel layer 34 may extend a predetermined distance over the edges 39 of the conductive layer 36. For example, in some embodiments, the predetermined distance that the gel layer 34 extends over the edges 39 of the conductive layer 36 may be greater than a thickness of the gel layer 34. This configuration of the gel layer 34 and conductive layer 36 avoids the edge effect and thus decreases the tingling or other uncomfortable sensations experienced by the subject.

Figure 14:
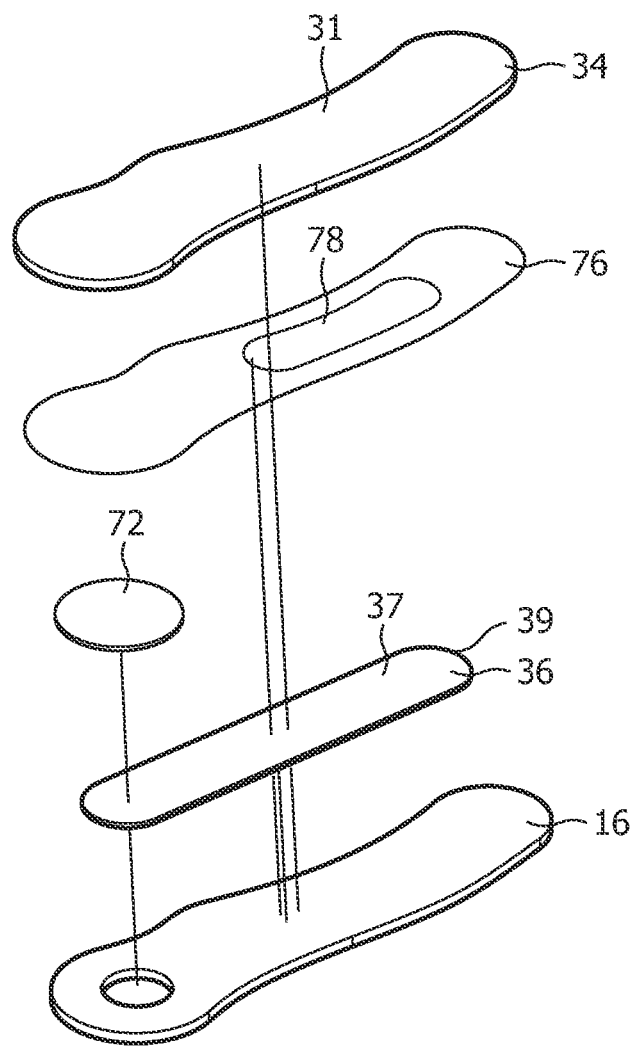
FIG. 14 illustrates an exploded view of another embodiment of the electrode.

FIG. 14 shows an exploded view of another embodiment of the electrode 14. In this embodiment, the electrode 14 includes the base pad 16. The conductive layer 36, which may be a current spreader configured to spread current through the electrode 14 and transmit electric signals to the subject's skin and/or receive electric signals from the subject's skin, may be disposed on the base pad 16. In the illustrated embodiment, the metal plate 72 is disposed on the conductive layer 36 and is positioned between the conductive layer 36 and the tape 76. Alternatively, the metal plate 72 may be positioned between the conductive layer 36 and the base pad 16. It is contemplated, however, that in some embodiments, the metal plate 72 may be replaced with magnetic material and the connector assembly 20 may have metal material. In the illustrated embodiment, the tape 76 is provided with the opening 78 configured to receive or overlap the conductive layer 36. The gel layer 34 may be disposed on the tape 76 such that the gel layer 34 may be electrically connected to the conductive layer 36 through the opening 78. In this embodiment, the first interface surface 31 of the gel layer 34 has a surface area larger than that of the first conductive surface 37 of the conductive layer 36. The footprint of the first interface surface 31 overlaps the entirety of a footprint of the first conductive surface 37. It is contemplated that an adhesive layer 38 (not shown in this Figure) may be positioned anywhere near the gel layer 34 and does not necessarily need to surround a periphery of the gel layer 34. The gel layer 34 may also include adhesive material to adhere the electrode 14 to the subject's skin. Adhesive material may be placed anywhere on the front layer 32. The base pad 16 may also optionally include adhesive material. The assembled electrode 14 of the embodiment of FIG. 14 is shown in FIG. 15.

In one embodiment, the electrode base pad 16 forms a generally flat back surface 28 (see FIG. 3b) on the side of the electrode 14 opposite the first interface surface 31. A detent 30 (see FIG. 7) may be formed in the flat back surface 28, and the first contact surface 18 of the electrode may be located in the detent 30. The detent 30 may be defined by the opening 70 (see FIG. 4) in the electrode base pad 16. The electrode base pad 16 may be made of non-conductive materials, such as paper, plastic, fabric, foam, other materials, or a combination thereof. The flat back surface 28 of the base pad 16 may optionally include adhesive material that enables the electrode base pad 16 to adhere to objects. Thus, the electrode 14 may optionally have adhesive material on both sides thereof.

The electrode 14 may include flexible material, thus enabling the electrode 14 to be generally flexible to conform to the contours of the subject's body.

Figure 7:
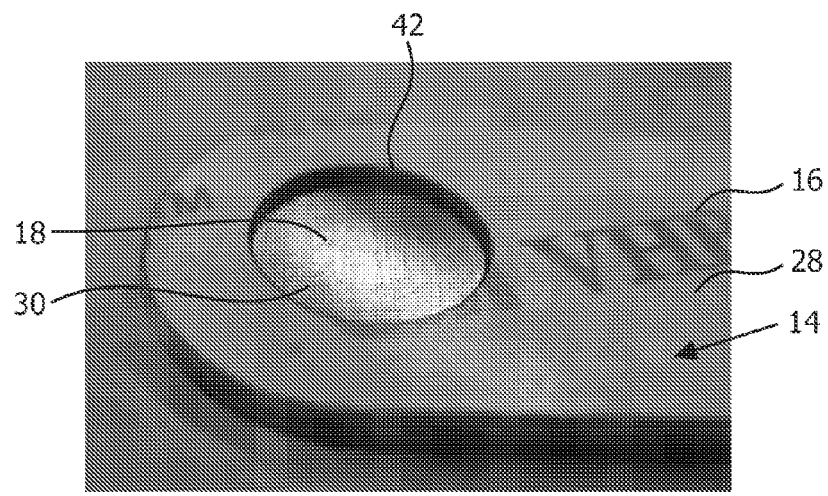
FIG. 7 illustrates a first contact surface of the electrode configured to contact a second contact surface of the connector assembly in accordance with one embodiment.

FIG. 7 is a detailed view of an embodiment of the electrode 14. As mentioned above, the first contact surface 18 is located in the detent 30. The detent 30 may be defined by the opening 70 (see FIG. 13) in the base pad 16. The opening 70 may be circular, rectangular, oval, or any other shapes. The first contact surface 18 is inset of the flat back surface 28 of the base pad 16. Thus, an edge 42 is formed around the periphery of the first contact surface 18. This configuration enables the second contact surface 24 (obstructed from view in this figure) of the connector assembly 20 to be easily aligned with the first contact surface 18 of the electrode 14. In particular, the inset of the first contact surface 18 relative to the flat surface of the flat back surface 28 enables the second contact surface 24 to be received in the detent 30, thus ensuring a proper electrical connection between the first contact surface 18 and the second contact surface 24. The edge 42 may prevent the second contact surface 24 from sliding away from its contact with the first contact surface 18. As such, this configuration facilitates and improves the positioning and alignment of the first contact surface 18 and the second contact surface 24. This configuration may also increase user comfort because of the lack of ridges, protrusions, and extra thickness in the electrode 14. Thus, the electrode 14 has a generally flat configuration that enables a subject to lie on it during use (e.g., during sleep).

The configuration of electrode 14 shown and described above with first contact surface 18 being the only first contact surface, and/or being disposed opposite first interface surface 31 is not intended to be limiting. For example, in one embodiment, electrode 14 includes a first contact surface formed on the same side of the electrode 14 as the first interface surface 31. This first contact surface formed on the same side of electrode 14 as the first interface surface 31 may replace the first contact surface 18 shown in the drawings and described above. The electrode 14 may include both of the first contact surface formed on the same side of electrode 14 as the first interface surface 31 and first contact surface 18 shown in the drawings and described above.

The second contact surface 24 is configured to be magnetically and electrically coupled to the first contact surface 18 of the electrode base pad 16. One or both of the first contact surface 18 and the second contact surface 24 may include a magnet. In one embodiment, either one of the first contact surface 18 or the second contact surface 24 may include a magnet and the other of the first contact surface 18 or the second contact surface 24 may include a metal material that is attracted to the magnet. Alternatively or additionally, the second contact surface 24 may be provided with a magnet. For example, the second contact surface 24 may be a magnet or the second contact surface 24 may be a metal material disposed on a magnet such that the second contact surface 24 may be magnetically and electrically coupled to the first contact surface 18 of the electrode base pad 16. Either one of the first contact surface 18 or the second contact surface 24 may include a ferromagnetic material, such as, just for example, iron, nickel, cobalt, rare earth metals, alloys (e.g., Alnico), or any combination thereof.

Referring back to FIG. 5, the connector assembly 20 has the attachment structure 21 in accordance with one embodiment. In the illustrated embodiment, the housing 22 of the attachment structure 21 is configured to hold the second contact surface 24. The second contact surface 24 is disposed in or on the housing 22. The housing 22 houses one or more components of the connector assembly 20 and is connected to the external electrical apparatus via an electrical connector 26. The housing 22 may be made of any suitable non-conductive material, including, just for example, any thermoplastic and/or elastomeric polymer such as polyvinyl chloride (PVC), thermoplastic polyurethanes, or fiber-reinforced polymer. The electrode base connector 26 may be an electrical cable or wire capable of transmitting electric signals, such as a lead wire. A connecting structure 40 (see FIG. 6) may be attached to the electrical connector 26 at an end opposite to that of the housing 22. The connecting structure 40 may be configured to releasably connect the connector assembly 20 to the external electrical apparatus. The connecting structure 40 may be a plug, terminal, or other similar structures that enable the connecting assembly 20 to be electrically connected to the external electrical apparatus.

Figure 8:
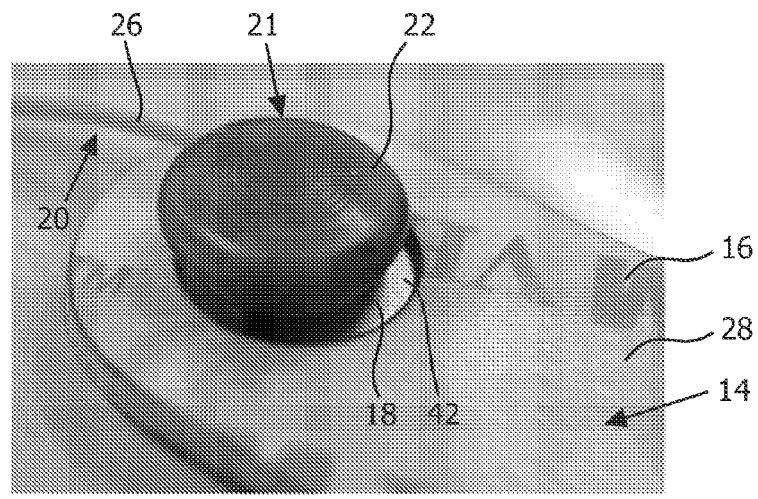
FIG. 8 illustrates a connection between the first contact surface of the electrode and the second contact surface of the connector assembly in accordance with one embodiment.

To establish an electrical connection between the subject's skin and the external electrical apparatus for delivering electrical stimulation to the subject, monitoring the physiological parameter of the subject, or both, the electrode can be connected to the subject's skin via the adhesive material on the front layer 32 of the electrode 14. In some embodiments, either one or both of the gel layer 34 and the adhesive layer 38 may provide the adhesive material used to adhere the electrode 14 to the subject's skin. Once the electrode 14 is adhered to the subject's skin, the first interface surface 31 defined by the gel layer 34 contacts the subject's skin and is electrically connected to the subject's skin. The connector assembly 20 can then be connected to the electrode 14 by magnetically coupling the first contact surface 18 of the electrode 14 with the second contact surface 24 of the connector assembly 20. As mentioned above, either one or both of the first contact surface 18 or the second contact surface 24 may include magnetic material or magnetized material. The second contact surface 24 may be slid along the flat back surface 28 until the second contact surface 24 is aligned with the detent 30 and the first contact surface 18, whereupon the second contact surface 24 magnetically and electrically couples with the first contact surface 18, as shown in FIG. 8. The second contact surface 24 can be operatively connected to the external electrical apparatus via the connector 26 of the connector assembly 20 or the connecting structure 40.

Figure 9A:
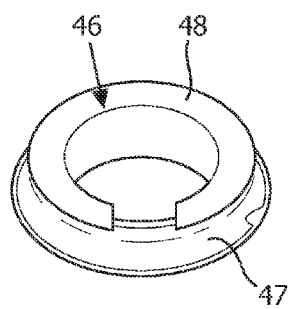
FIGS. 9a-9e illustrate components of the attachment structure of the connector assembly in accordance with an embodiment.
Figure 9B:
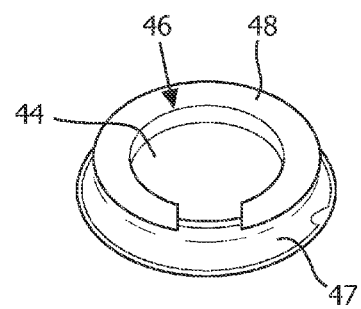

FIGS. 9a-9e illustrate components of the attachment structure 21 of the connector assembly 20 in accordance with an embodiment. In this embodiment, the second contact surface 24 is defined on a permanent magnet. In one exemplary embodiment, the magnet is a Neoflux® magnet. As shown in FIG. 9b, a magnetic material 44 is attached to a metal conductor 46 having a circular configuration. A groove 47 may be provided on the periphery of the metal conductor 46. The magnetic material 44 may be received in the metal conductor 46 such that the metal conductor 46 forms a periphery around the magnetic material 44. The magnetic material 44 may be attached to the metal conductor 46 via adhesives or other attachment mechanisms. The magnetic material 44 may be inset from the metal conductor 46. That is, the top surface of the magnetic material 44 may be situated below the top surface 48 of the metal conductor 46. In one embodiment, the top surface of the magnetic material 44 may be inset from the top surface 48 of the metal conductor 46 by about 0.5 mm. In some embodiments, this configuration of the magnetic material 44 in the attachment structure 21 enables the magnetic material 44 to be at an elevated height with respect to the flat back surface 27 of the base pad 16 when the first contact surface 18 is magnetically coupled to the second contact surface 24. In other words, this configuration of the magnetic material 44 enables the magnetic material 44 to be outside of the detent 30 while the second contact surface 24 is in the detent 30 and is coupled to the first contact surface 18 of the electrode 14. However, it is contemplated that the magnetic material 44 may be positioned in the attachment structure 21 such that the magnetic material 44 is in the detent 30 while the second contact surface 24 is also in the detent 30 and is coupled to the first contact surface 18 of the electrode 14.

Figure 9C:
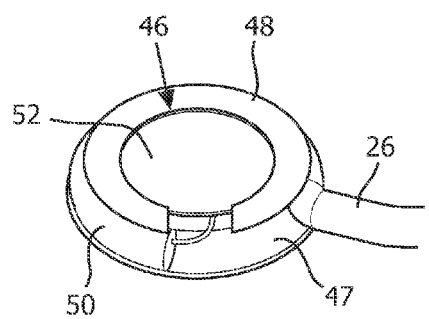
Figure 9D:
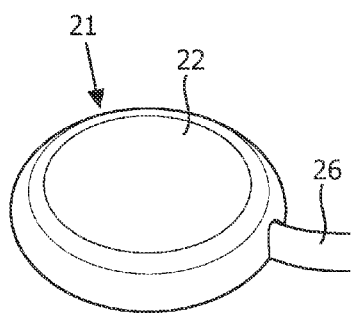
Figure 9E:
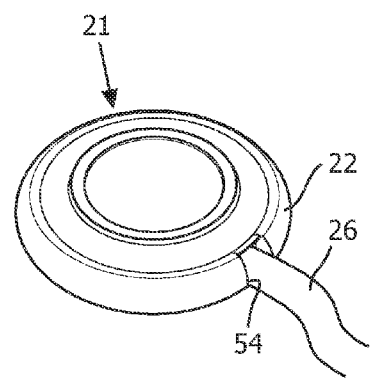

As shown in FIG. 9c, an electrical connector, such as an electrical wire 50, may be provided in the groove 47 around the periphery of the metal conductor 46. An end of the electrical wire 50 may be connected to the magnetic material 44 via a conducting adhesive, soldering, or other attachment mechanisms. In one embodiment, the electrical wire 50 may be connected to the top surface of the magnetic material 44. A conductive structure, taking the form of a plate 52 in this embodiment, is placed on top of the magnetic material 44 such that the end of the electrical wire 50 is disposed between the plate 52 and the magnetic material 44. In one embodiment, the electrical wire 50 may be integral to the electrical connector 26. Alternatively, the electrical wire 50 may optionally be a separate wire that is electrically connected to the electrical connector 26. The housing 22 may be placed over the metal conductor 46, plate 52, and magnetic material 44, as shown in FIGS. 8d-8e, to form the attachment mechanism 21. The connector 26 may extend through a groove 54 provided in the housing 22. When the housing 22 is attached to the metal conductor 46, a portion of the housing 22 may be received in the groove 47 of the metal conductor 46. In some embodiments, the coupling between wire 50 with the metal conductor 46 may be releasable. This may enhance the comfort of the subject, as forces that could cause discomfort to the subject may simply result in disconnection between wire 50 and conductor 46. By way of non-limiting example, wire 50 may be wrapped around the metal conductor 46 in the groove 47 to form a releasable friction interface between wire 50 and metal conductor 46. This may enable the coupling arrangement to be more compact. However, it is contemplated that in some embodiments, the coupling between wire 50 and metal conductor 46 is not releasable.

Figure 10:
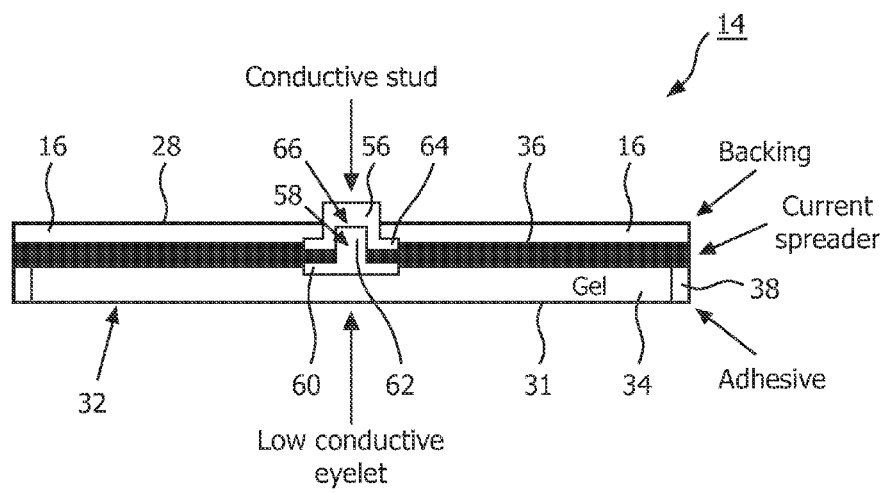
FIG. 10 illustrates a cross sectional view of an electrode having a low conductivity portion in accordance with an embodiment.

FIG. 10 shows a cross section of another embodiment of the electrode 14. In this embodiment, the electrode 14 includes several layers of materials, such as the front layer 32 defined by the gel layer 34 and the adhesive layer 38. In this embodiment, the adhesive layer 38 is provided with adhesive material to facilitate the connection between the electrode 14 and the subject's skin. The conductive layer 36 is provided between the first interface surface 31 defined by the gel layer 34 and the flat back surface 28 of the base pad 16. A conductive stud 56 is also provided, wherein the conductive stud 56 is configured to engage in a snap-fit connection with the receiving portion (not shown) of another embodiment of the connector assembly 20. In the illustrated embodiment of the electrode 14, an eyelet 58 is configured to be fixed to the stud 56. In this embodiment, the stud 56 may be considered the first contact surface 18. That is, in some embodiments that have the stud 56, the stud 56 may be magnetically coupled to a portion of the connector assembly 20. In embodiments wherein the electrode 14 is used for stimulation purposes, the stud 56 may receive electric signals from the connector assembly 20 and conduct the electric signals to the conductive layer 36, which distributes the electric signals to the gel layer 34. The gel layer 34 may then distribute the electric signals to the subject's skin.

In the illustrated embodiment, the eyelet 58 has a head 60 in contact with the conductive layer 36 and the gel layer 34. Additionally, the eyelet 58 has a shaft 62 that extends through the conductive layer 36 and into the base pad 16. In the illustrated embodiment, the stud 56 has a head 64 that contacts the conductive layer 36 and the base pad 16. Additionally, the stud 56 has a shaft 66 that extends through and out of the base pad 16 so that the stud 56 may be engaged in a snap-fit connection with the connector assembly 20. The eyelet 58 may also optionally be friction fitted, riveted or crimped into the stud 56. As mentioned above, if the eyelets 58 are made of conductive materials, such as metal or covered with metallic conductive materials, this configuration may create "hot spots" due to the highly conductive nature of the eyelets 58 and due to uneven electrode-skin contact. For example, if the eyelet 58 is constructed from highly conductive materials, the shorter distance between the head 60 of the eyelet 58 and the subject's skin relative to the distance between the conductive layer 36 and the subject's skin may cause uneven current distribution and "hot spots".

In the embodiment shown in FIG. 10, the eyelet 58 includes materials having a lower conductivity than that of metals, such as, for example, plastic. In some embodiments, the eyelet 58 includes non-conductive materials. In one embodiment, the eyelet 58 is a carbon-filled plastic eyelet. The stud 56 may be made of conductive materials, such as metal. In one embodiment, the stud 56 is made of a metal material having silver coating. Thus, in this embodiment, the eyelet 58 has a lower conductivity than that of the stud 56 and the conductive layer 36. This configuration and characteristics of the eyelet 58 and the stud 56 may eliminate high current density at the position of the eyelet 58, thus avoiding "hot spots".

Figure 11:
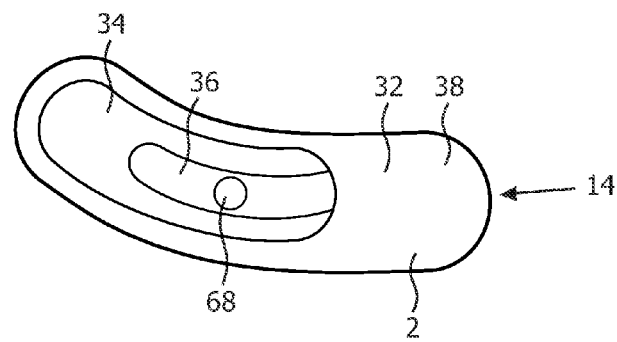
FIG. 11 illustrates the low conductivity portion of the electrode in accordance with an embodiment.

In the embodiment shown in FIG. 11, the conductive layer 36 includes a low conductive portion 68 having an area smaller than that of the conductive layer 36. The low conductive portion 68 may comprise a material having a lower conductivity than that of the rest of the conductive layer 36. In one embodiment, the low conductive portion 68 may be disposed within the conductive layer 36 or may be a separate piece attached to the conductive layer 36. In one embodiment, the conductive layer 36 may surround the low conductive portion 68 such that the low-conductivity portion 68 is situated like an "island" within or on the conductive layer 36. In one embodiment, the low conductive portion 68 may cover the conductive layer 36 similar to the head 60 of the eyelet 58 shown in FIG. 10. Accordingly, the low conductive portion 68 may reduce the chances of or avoid the occurrence of "hot spots." In one embodiment, the low conductive portion 68 may be made of plastic. The size, shape, or configuration of the low conductive portion 68 may vary.

Figure 12:
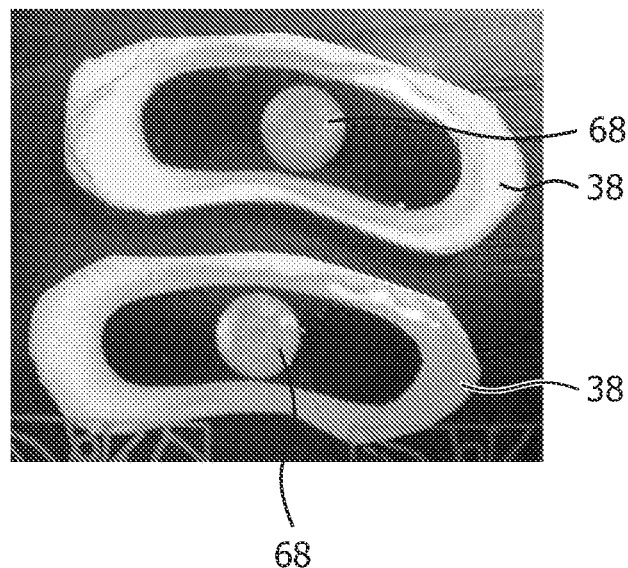
FIG. 12 illustrates low-conductivity or non-conductive portions of the electrode in accordance with one embodiment.

As shown in FIG. 12, the electrode 14 may have non-conductive or low-conductive portions, including the adhesive layer 38 and the low-conductive portion 68. In embodiments where the electrode 14 includes the stud 56 and the eyelet 58, the low-conductive portion 68 may be the eyelet 58. Alternatively, the low-conductive portion 68 may be a portion of the conductive layer 36 that is either non-conductive or has low-conductive properties. The low-conductive portion 68 may be a low conductive material within the conductive layer 36 or may be attached to the conductive layer 36.

Figure 13:
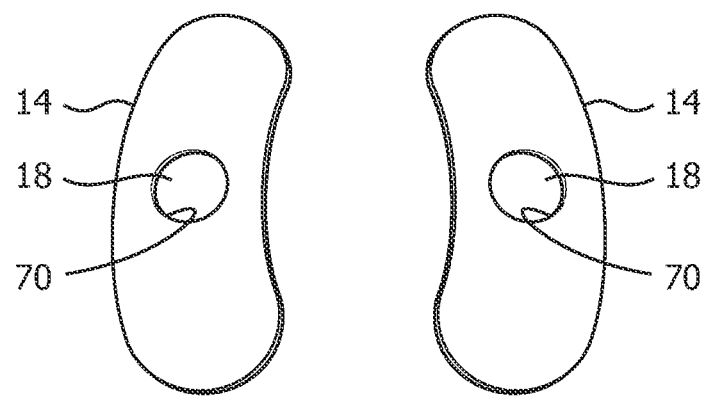
FIG. 13 illustrates the base pad opposite the side of the electrode having the subject contact surface, in accordance with an embodiment.

FIG. 13 shows an embodiment of the electrode 14. In this embodiment, the opening 70 and the first contact surface 18 is located centrally of the base pad 16. It is contemplated that the opening 70 may be located at other locations and may vary in size and location.

The size, shape, and configuration of the electrode 14 may vary in various embodiments. For example, in one embodiment, the electrode 14 may include more than one first contact surface 18. As such, a plurality of attachment structures 21 of the connector assembly 20 may be used to create connections between the connector assembly 20 and the first contact surfaces 18 of the electrode 14. In some embodiments, a plurality of connector assemblies 20 may be connected to a single electrode 14 that has a plurality of first contact surfaces 18.

It is also contemplated that one or more sensors may be provided on the electrodes 14. For example, a temperature sensor, motion sensors, microphone, oximetry sensor, or any combination thereof can be provided for detecting various physiological parameters of the user. The output of these sensors can be used to control the stimulation therapy provided to the user, stored for monitoring purposes, transmitted to a remote location, or any combination thereof. It is also contemplated that in some embodiments, the one or more sensors may be provided on the connector assembly 20. The connector assembly 20 may be connected to the external electrical apparatus wirelessly instead of using a wire. In such wireless embodiments, electric signals and information may be transferred between the connector assembly 20 and the external electrical apparatus wirelessly, such as via RF frequency, IR frequency, or other frequencies. In such embodiments, the connector assembly 20 may include a power source and/or a transceiver. Accordingly, in such embodiments, the transceiver may be considered the electrical connector 26. The connector assembly 20 and the electrode 14 may transfer signals between each other via the magnetic and electrical coupling, as described above.

The electrode assembly 13 may be used in a variety of ways and are not limited to the ones described. It is contemplated that the electrode assembly 13 can be used to deliver energy, monitor one or more of a variety of physiological parameters of the subject, such as electro-physiological impedance signals, physiological resistance, or any combination thereof. Other parameters that can be monitored include galvanic skin responses and ear-to-ear impedance changes.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An electrode configured to provide electrical contact with a subject's skin and to transmit electrical signals from the subject's skin to an external electrical apparatus, wherein the electrode is further configured to receive electrical signals from the external electrical apparatus for transfer to the subject's skin, the electrode comprising:
 a base pad configured to provide electrical insulation, wherein the base pad includes an opening;
 a conductive layer configured to spread current and transfer the electrical signals, the conductive layer having a first conductive surface through which the electrical signals are transferred, the first conductive surface being on a side of the conductive layer that faces toward the skin of the subject if the electrode is installed on the subject;
 a plate configured to transmit the electrical signals, wherein the plate includes ferromagnetic material configured to magnetically couple with the external electrical apparatus, the plate being arranged on the side of the conductive layer that faces toward the skin of the subject if the electrode is installed on the subject, wherein the conductive layer is arranged between the base pad and the plate;

electrically insulating material configured to provide electrical insulation, wherein the electrically insulating material includes a second opening, the electrically insulating material being arranged on the side of the conductive layer that faces toward the skin of the subject if the electrode is installed on the subject, wherein the plate is arranged between the conductive layer and the electrically insulating material;

a gel layer configured to conduct the electrical signals between the subject's skin and the external electrical apparatus, the gel layer being arranged on the side of the conductive layer that faces toward the skin of the subject if the electrode is installed on the subject, wherein the electrically insulating material is arranged between the plate and the gel layer, wherein the electrical signals received from the external electrical apparatus are transmitted through the opening of the base pad, through the conductive layer, through the second opening in the electrically insulating material, through the gel layer, and to the subject's skin.

2. The electrode of claim 1, further comprising an adhesive layer configured to be disposed between the conductive layer and the subject's skin, the adhesive layer being configured to contact and adhere to the subject's skin.

3. The electrode of claim 2, wherein the adhesive layer generally surrounds a periphery of the gel layer.

4. The electrode of claim 1, wherein the gel layer and the conductive layer are formed such that a footprint of the gel layer overlaps the entirety of a footprint of the first conductive surface.

5. The electrode of claim 1, wherein the opening of the base pad is positioned relative to the second opening of the electrically insulating material such that the opening and the second opening are entirely non-overlapping.

6. An electrode configured to provide electrical contact with a subject's skin and to transmit electrical signals from the subject's skin to an external electrical apparatus, wherein the electrode is further configured to receive electrical signals from the external electrical apparatus for transfer to the subject's skin, the electrode comprising:

first means for electrically insulating, wherein the first means for electrically insulating includes an opening;

means for spreading current and transferring the electrical signals, the means for spreading current having a first conductive surface configured to transfer the electrical signals, the first conductive surface being on a side of the means for spreading current that faces toward the skin of the subject if the electrode is installed on the subject;

means for transmitting the electrical signals, wherein the means for transmitting the electrical signals includes ferromagnetic material configured to magnetically couple with the external electrical apparatus, the means for transmitting the electrical signals being arranged on the side of the means for spreading current that faces toward the skin of the subject if the electrode is installed on the subject, wherein the means for spreading current is arranged between the first means for electrically insulating and the means for transmitting the electrical signals;

second means for electrically insulating, wherein the second means for electrically insulating includes a second opening, the second means for electrically insulating being arranged on the side of the means for spreading current that faces toward the skin of the subject if the electrode is installed on the subject, wherein the means for transmitting the electrical signals is arranged between the means for spreading current and the second means for electrically insulating; and means for conducting the electric signals between the subject's skin and the first conductive surface, the means for conducting the electric signals being arranged on the side of the means for spreading current that faces toward the skin of the subject if the electrode is installed on the subject, wherein the second means for electrically insulating is arranged between the means for transmitting the electrical signals and the means for conducting the electrical signals, wherein the electrical signals received from the external electrical apparatus are transmitted through the opening of the first means for electrically insulating, through the means for spreading current, through the second opening of the second means for electrically insulating, through the means for conducting the electric signals, and to the subject's skin.

7. The electrode of claim 6, further comprising adhesive means for contacting and adhering the electrode to a subject's skin, the adhesive means being arranged on the side of the means for spreading current that faces toward the skin of the subject if the electrode is installed on the subject.

8. The electrode of claim 7, wherein the adhesive means generally surrounds a periphery of the means for conducting the electrical signals.

9. The electrode of claim 6, wherein the means for conducting the electrical signals and the means for spreading current are formed such that a footprint of the means for conducting the electrical signals overlaps the entirety of a footprint of the first conductive surface.

10. The electrode of claim 6, wherein the opening of the first means for electrically insulating is positioned relative to the second opening of the means for electrically insulating such that the opening and the second opening are entirely non-overlapping.

11. A method of manufacturing an electrode for providing electrical contact with a subject's skin, the electrode being configured to transmit electrical signals from the subject's skin to an external electrical apparatus, the electrode further being configured to receive electrical signals from the external electrical apparatus for transfer to the subject's skin, the method comprising:

forming a base pad to provide electrical insulation, wherein the base pad has an opening;

forming a conductive layer configured to spread current and transfer the electrical signals, wherein the conductive layer is formed such that the conductive layer has a first conductive surface through which the electrical signals are transferred, the first conductive surface being on a side of the conductive layer that faces toward the skin of the subject if the electrode is installed on the subject;

forming a plate to transmit the electrical signals, wherein the plate includes ferromagnetic material, the plate being arranged on the side of the conductive layer that faces toward the skin of the subject if the electrode is installed on the subject;

forming electrically insulating material to provide electrical insulation, the electrically insulating material being arranged on the side of the conductive layer that faces toward the skin of the subject if the electrode is installed on the subject, wherein the electrically insulating material includes a second opening;

forming a gel layer to conduct the electrical signals between the subject's skin and the external electrical apparatus, the gel layer being arranged on the side of the conductive layer that faces toward the skin of the subject if the electrode is installed on the subject;

arranging the conductive layer between the base pad and the plate;

arranging the plate between the conductive layer and the electrically insulating material; and arranging the electrically insulating material between the plate and the gel layer, wherein the electrical signals received from the external electrical apparatus are transmitted through the opening of the base pad, through the conductive layer, through the second opening in the electrically insulating material, through the gel layer, and to the subject's skin.

12. The method of claim 11, further comprising forming an adhesive layer configured to contact and adhere to the subject's skin, wherein the adhesive layer is further configured to be arranged between the conductive layer and the subject's skin.

13. The method of claim 12, wherein forming the adhesive layer includes generally surrounding a periphery of the gel layer.

14. The method of claim 11, wherein the gel layer and the conductive layer are formed such that a footprint of the gel layer overlaps the entirety of a footprint of the first conductive surface.

15. The method of claim 11, wherein arranging the electrically insulating material includes positioning the second opening of the electrically insulating material relative to the opening of the base pad such that the opening and the second opening are entirely non-overlapping.

\* \* \* \* \*